(12) United States Patent
Sogaro

(10) Patent No.: US 6,613,021 B2
(45) Date of Patent: Sep. 2, 2003

(54) AMPOULE FOR DISPENSING A SUBSTANCE OR A MIXTURE OF A PLURALITY OF SUBSTANCES

(75) Inventor: Alberto C. Sogaro, Kronberg (DE)

(73) Assignee: Dentaco Dentalindustrie und-marketing GmbH, Bad Homburg (DE)

( * ) Notice: Subject to any disclaimer, the term of this patent is extended or adjusted under 35 U.S.C. 154(b) by 0 days.

(21) Appl. No.: 10/001,706

(22) Filed: Oct. 31, 2001

(65) Prior Publication Data

US 2002/0052579 A1 May 2, 2002

(30) Foreign Application Priority Data

Nov. 2, 2000 (WO) .............................. PCT/EP00/10778
May 2, 2001 (DE) ......................... 201 07 507

(51) Int. Cl.[7] ............................................ A61M 37/00
(52) U.S. Cl. ........................................ 604/191; 604/89
(58) Field of Search ................................ 604/218, 238, 604/236, 190, 240, 241, 231, 89, 82, 90, 91, 167.03, 237, 191

(56) References Cited

U.S. PATENT DOCUMENTS

| 2,168,686 A | 8/1939 | Saffir ........................... 128/218 |
| 2,871,857 A | 2/1959 | Lipari et al. ................. 128/218 |
| 3,330,280 A | * 7/1967 | Ogle |
| 3,572,336 A | 3/1971 | Hershberg ................... 128/218 |
| 4,303,069 A | 12/1981 | Cohen ........................... 128/218 |
| 4,596,561 A | 6/1986 | Meyer et al. ............... 604/190 |
| 4,610,666 A | 9/1986 | Pizzino ........................ 604/191 |
| 5,478,321 A | 12/1995 | Kimber ........................ 604/187 |
| 5,496,284 A | * 3/1996 | Waldenburg ................. 604/191 |
| 6,149,628 A | * 11/2000 | Szapiro et al. ............... 604/191 |

FOREIGN PATENT DOCUMENTS

| CH | 414 953 A | 6/1966 | ............ A61M/5/00 |
| DE | 29919291 U | 12/2000 | ............ A61M/5/28 |
| FR | 2 070 358 | 9/1971 | ............ A61M/5/00 |
| WO | 99 17833 A | 4/1999 | .......... A61M/37/00 |
| WO | WO9917833 | 4/1999 | .......... A61M/37/00 |
| WO | 01 54758 | 8/2001 | ............ A61M/5/32 |

* cited by examiner

*Primary Examiner*—Sharon Kennedy
(74) *Attorney, Agent, or Firm*—Quarles & Brady LLP

(57) ABSTRACT

Ampoule for dispensing a substance comprising: a container having a chamber therein for storing a substance to be dispensed; a piston arranged in the chamber so as to be displaceably in longitudinal correction of the chamber; an outlet means which can be connected to the container such that a fluid communication is established between an inlet portion of a discharge passage of the outlet means and an outlet opening of the chamber; and a plug closure means being insertable in a fluid-tight manner into the outlet opening of the chamber and, when it has been fluid-tightly inserted into the outlet opening, being displaceable by the outlet means connected to the container in direction towards the interior of the chamber from a closed position into an open position in which a fluid communication is provided between the interior of the chamber and the inlet portion of the discharge passage of the outlet means via the outlet opening of the chamber, the plug closure means having retaining means retaining the plug closure means in the open position.

11 Claims, 5 Drawing Sheets

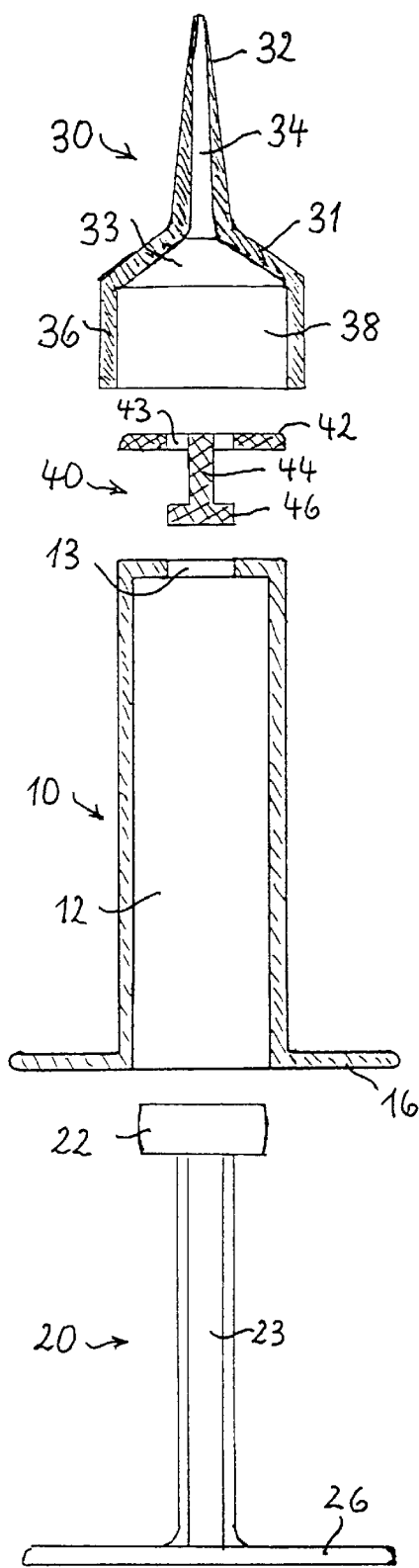
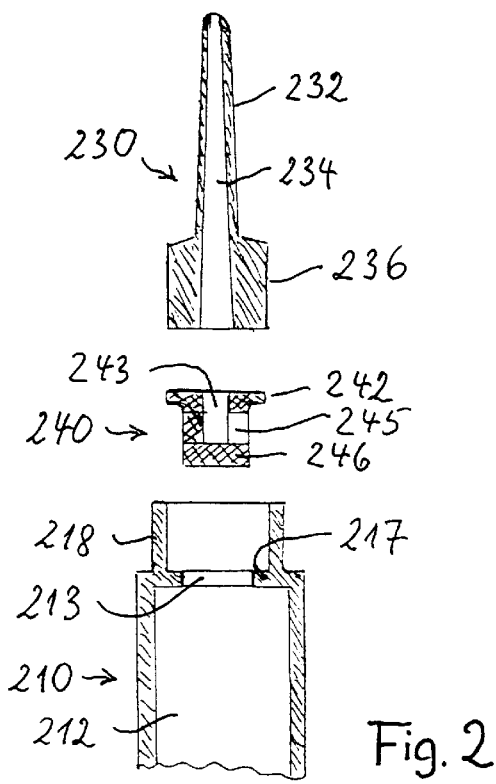
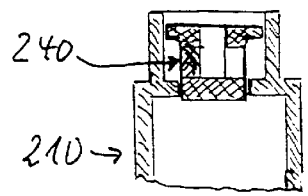
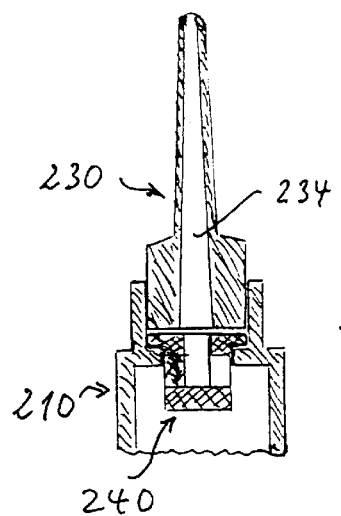
Fig. 1
Fig. 2
Fig. 3
Fig. 4

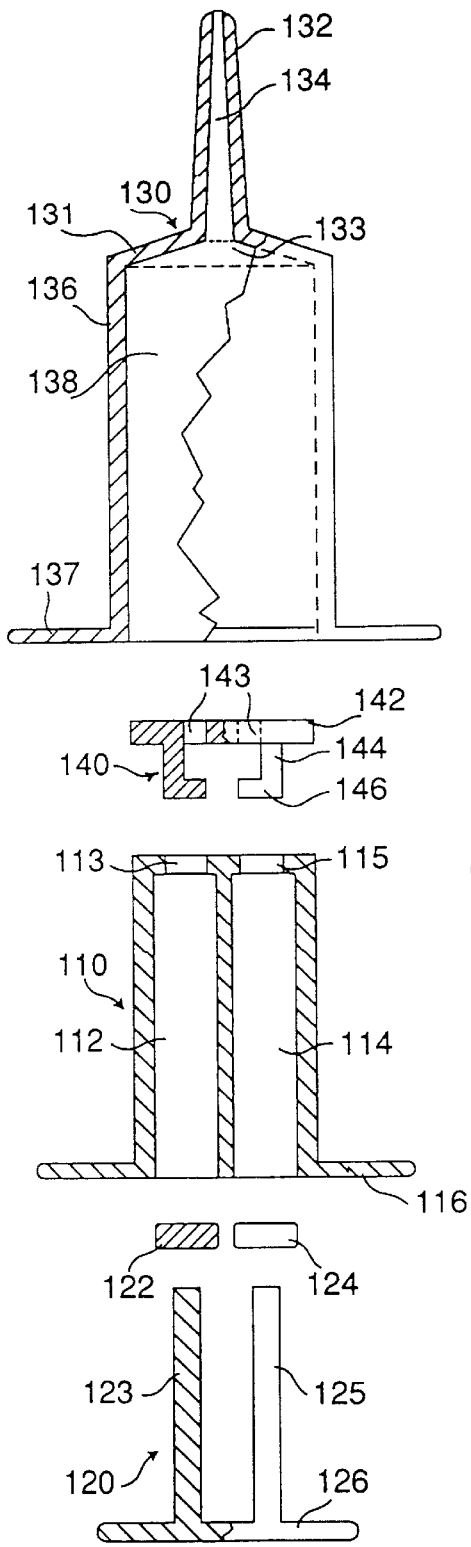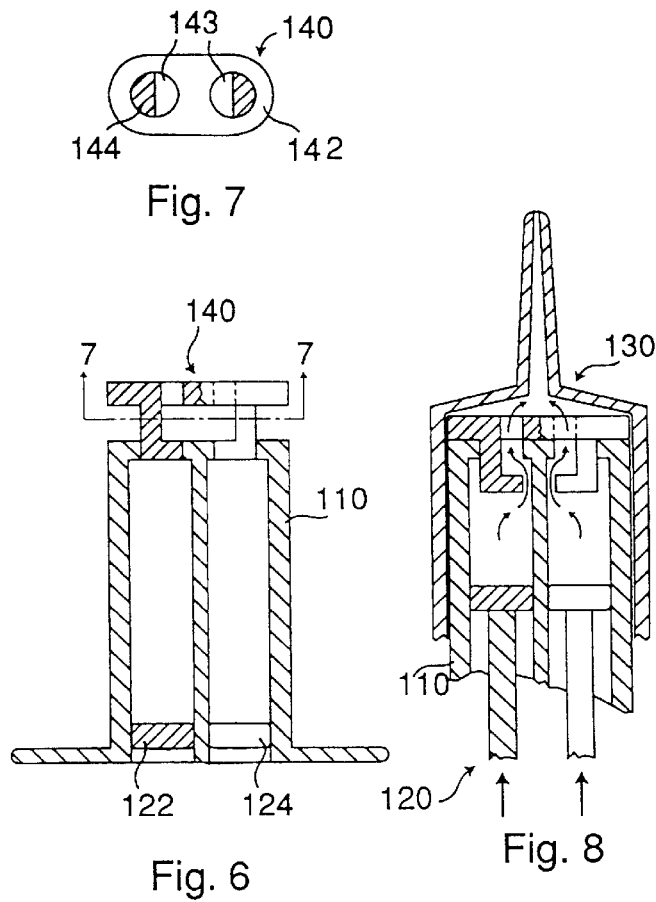
Fig. 5  Fig. 6  Fig. 7  Fig. 8

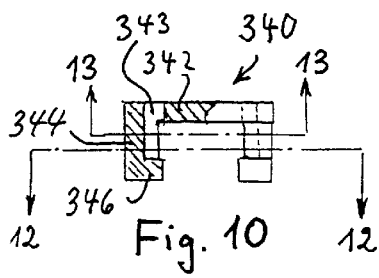
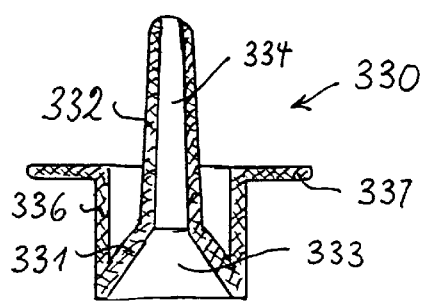
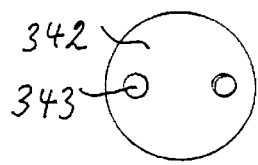
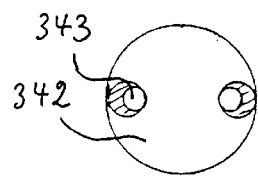
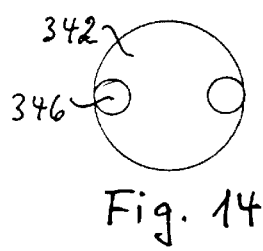
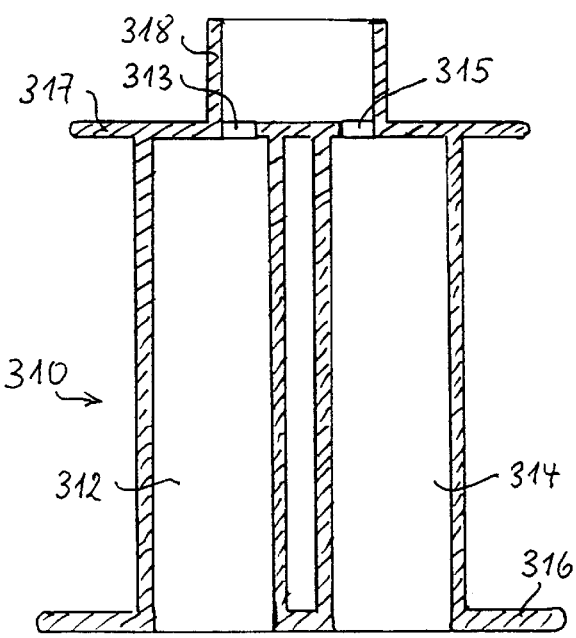
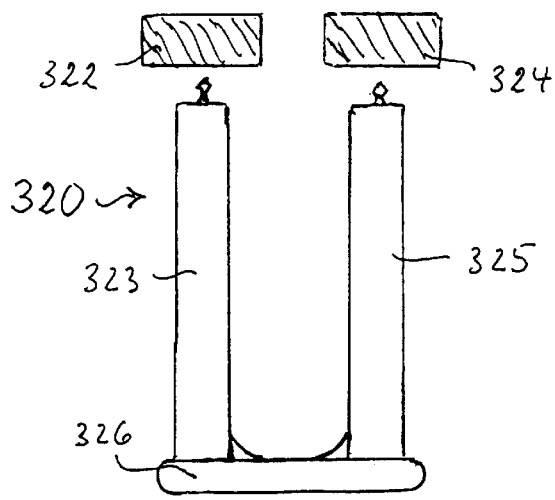

AMPOULE FOR DISPENSING A SUBSTANCE OR A MIXTURE OF A PLURALITY OF SUBSTANCES

CROSS REFERENCES TO RELATED APPLICATIONS

This application claims the priority benefit of PCT Application PCT/EP00/10778 filed on Nov. 2, 2000 and German Patent Application DE 201 07 507.5 filed on May 2, 2001.

STATEMENT REGARDING FEDERALLY SPONSORED RESEARCH

Not Applicable

BACKGROUND OF THE INVENTION

The present invention concerns an ampoule for dispensing a substance or a mixture consisting of a plurality of substances. In the field of medicine and cosmetics, as well as, in other fields, it is often necessary to separately store the individual components of a multicomponent-product. Furthermore, it is often necessary that the individual components are mixed with one another only just before the application. Moreover, it is often necessary or at least desirable to store the individual components as fluid-tight or liquid-tight as possible. This also holds true in case of systems for dispensing only a single substance.

French Patent Application No. FR 2 070 358 A shows an injection syringe for a single use. The syringe has a cylindrical body filled with a substance to be injected. The rear end of the body filled with the substance is closed by means of a piston which is displaceable in the longitudinal direction of the syringe body. The discharge opening at the front end of the syringe body is shut off by means of a plug which is displaceable within the discharge opening. In a first embodiment of the prior art injection syringe, the plug is a relatively short solid body. For activating the syringe the plug is pushed completely out of the discharge opening into the syringe body by means of an injection needle being displaceably mounted to the syringe body. In an alternative solution, the plug is pushed completely out of the discharge opening into a pre-chamber joining the syringe body by applying pressure by means of the piston. The injection needle is fixedly connected to this pre-chamber. It is disadvantageous that the plug, after having been injected from the discharge opening, freely swims within the syringe body or within the pre-chamber and, hence, can impede the discharge of the substance to be injected.

In a further embodiment of the prior art injection syringe, the plug is fixedly connected to the injection needle and the unity of the plug and injection needle is guided within a pre-chamber adjacent to the syringe body. It is disadvantageous that the plug and the injection needle form a one-piece member which, already when producing the injection syringe, has to be mounted to the syringe body. Furthermore, it can be disadvantageous during transport or storage of the prior art injection syringe that the plug as well as the injection needle fixedly connected to the plug protrude beyond the syringe body.

U.S. Pat. No. 3,572,336 A discloses an injection syringe which is manipulated by means of spring action. The syringe comprises a syringe body having a plurality of cylindrical chambers being arranged in parallel to one another. Each chamber is filled with a respective substance. The filled chambers are each closed by a piston of a common piston unit at their rear ends. The discharge openings provided at the front end of the syringe body are covered in a fluid-tight manner with a common membrane. Upon application of the syringe the pistons of the piston unit are pushed forward into the chambers when releasing a compressed spring. Thereby, the membrane at the discharge openings of the chambers ruptures and the substances contained in the chambers reach a mixing chamber via the discharge openings freed from the membrane. The substances are then expelled via an injection needle being fixedly connected to the mixing chamber. This prior art syringe has a complicated construction and production thereof is sophisticated.

BRIEF SUMMARY OF THE INVENTION

It is an object of the invention to provide an ampoule for dispensing a substance or mixture of a plurality of substances being designed in a simple manner and which can be easily handled. Furthermore, the ampoule should offer the possibility to store one or a plurality of substances to be dispensed separately from one another. The ampoule according to the invention is particularly designed for a single use.

According to a first aspect of the invention an ampoule for dispensing a substance comprises: a container having a chamber therein for storing a substance to be dispensed; a piston arranged in the chamber so as to be displaceably in the longitudinal direction of the chamber; an outlet means which can be connected to the container such that a fluid communication is established between an inlet portion of a discharge passage of the outlet means and an outlet opening of the chamber; and a plug closure means being insertable in a fluid-tight manner into the outlet opening of the chamber and, when it has been fluid-tightly inserted into the outlet opening, being displaceable by the outlet means connected to the container in direction towards the interior of the chamber from a closed position into an open position in which a fluid communication is provided between the interior of the chamber and the inlet portion of the discharge passage of the outlet means via the outlet opening of the chamber, the plug closure means having retaining means retaining the plug closure means in the open position.

According to a second aspect of the present invention there is provided a multichamber-ampoule for dispensing a mixture consisting of a plurality of substances and comprising: a container having at least two chambers therein being arranged in parallel to each other for storing the substances and having adjacent outlet openings; a piston provided in each chamber so as to be displaceable in longitudinal direction of the chamber; an outlet means which can be connected to the container such that a fluid communication is established between the outlet openings of the chambers and an inlet portion of a discharge passage of the outlet means; and a plurality of plug closure means corresponding to the plurality of outlet openings of the chambers, each plug closure means being insertable in a fluid-tight manner into its associated outlet opening and, when the plug closure means have been fluid-tightly inserted into the outlet openings, they are displaceable by the outlet means connected to the container in direction towards the interior of their associated chambers from a closed position into an open position in which a fluid communication is provided between the interior of the chambers and the inlet portion of the discharge passage of the outlet means via the outlet opening of the chamber, the plug closure means having retaining means retaining the plug closure means in the open position.

The retaining means guarantee that the plug closure means do not fall into the substance containing chambers when the ampoule has been activated. They can be provided as radially extending means which, for example, protrude beyond the outlet opening of a chamber.

The ampoule according to the invention offers the advantage that merely a minimum of component parts are necessary for implementing the ampoule. Furthermore, these components parts are easily produceable and the component parts can be assembled in an easy manner. Nevertheless, the ampoule can be readily handled and offers a reliable application. For activating the ampoule, it is merely necessary to displace the outlet means in the direction of the substance container until these two components of the ampoule engage one another where upon the or each one of the outlet openings of the single chamber or the plurality of chambers are cleared and the plug closure is retained between the outlet means and the substance container in this open position.

According to a further aspect of the present invention, the invention comprises a unit merely consisting of the container, the piston and a plug closure means.

According to another aspect of the present invention, the invention is directed to the plug closure means as such.

These and other objects and advantages of the invention will herein after be described by referring to preferred embodiments of the invention shown in the accompanying drawings.

BRIEF DESCRIPTION OF THE DRAWINGS

FIG. 1 is a partially sectional exploded view of a first embodiment of the invention;

FIG. 2 is a sectional exploded view of essential components of a second embodiment of the invention;

FIG. 3 is a sectional partial view of the second embodiment according to FIG. 2 in closed state;

FIG. 4 is a sectional partial view of the second embodiment according to FIG. 2 in activated and open state;

FIG. 5 is a partially sectional exploded view of a third embodiment of the invention;

FIG. 6 is a partially sectional view of a substance container of the third embodiment according to FIG. 5 in closed state;

FIG. 7 is a sectional view of a closure means used in the third embodiment taken along a line 7—7 in FIG. 6;

FIG. 8 is a partially sectional and broken-away view of a third embodiment in activated and open state;

FIG. 9 is a partially sectional exploded view of fourth embodiment of the invention;

FIG. 10 is a partially sectional view of a closure means used in the fourth embodiment according to FIG. 9;

FIG. 11 is a view onto the closure means of FIG. 10 from above;

FIG. 12 is a sectional view of the closure means according to FIG. 10 taken along a line 12—12 in FIG. 10;

FIG. 13 is a sectional view of the closure means according to FIG. 10 taken along a line 13—13 in FIG. 10;

FIG. 14 is a bottom view of the closure means according to FIG. 10;

DETAILED DESCRIPTION OF THE PREFERRED EMBODIMENTS

Figures 15, 16:
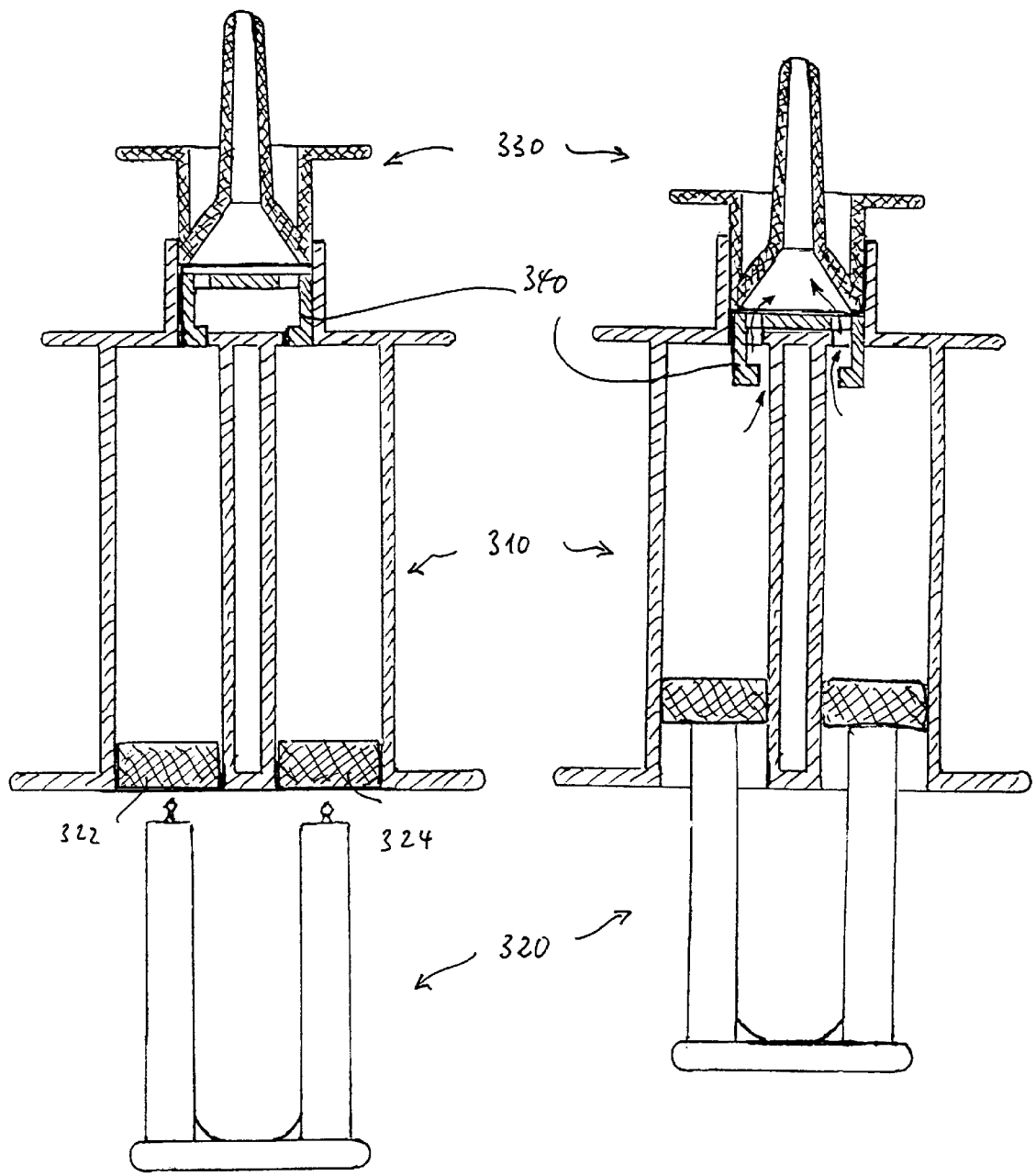
FIG. 15 is a partially sectional view of the fourth embodiment according to FIG. 9 in closed state.
FIG. 16 is a partially sectional view of the fourth embodiment according to FIG. 9 in activated and open state.

The first embodiment shown in FIG. 1 is an ampoule which generally consists of four components, namely a container 10, a piston unit 20, an outlet piece 30 and a closure means 40. The container 10 comprises an inner cylindrical chamber 12 which extends in the longitudinal direction of the container 10. Chamber 12 is open at its rear end and has a discharge opening 13 at its front end.

The piston unit 20 comprises a circular cylindrical piston 22, a piston rod 23 and a plate 26 integrally connected to the rear end of the piston rod 23. The outer diameter of the piston 22 substantially corresponds to the inner diameter of the circular cylindrical cross section of chamber 12 so that the piston 22 after having been inserted into chamber 12 engages the chamber wall as tight as possible, particularly fluid-tight, whereas the piston is still displaceable in longitudinal direction of chamber 12.

The outlet piece 30 consists of a front portion 32 and a rear portion 36. The front portion 32 is formed in a tube-like configuration and surrounds a discharge passage 34 with a relatively small circular cross section. The rear portion 36 of outlet piece 30 has a substantially larger diameter than the front portion 32 and it defines a cylindrical inner space 38. The inner space 38 is open at its rear end and merges at its front end into the discharge passage 34. The likewise cylindrical container 10 has an outer diameter which essentially corresponds to the inner diameter of hollow space 38 so that the container 10 after having been inserted into the hollow space 38 engages with its outer wall the circumferential wall defining the inner space 38 of the outlet piece 30. This engagement is as tight as possible, particularly fluid-tight. The outlet piece 30 has a sloped shoulder 31 extending between the front portion 32 and the rear portion 36 of the outlet piece 30 and defining a space 33 in form of a shallow truncated cone or frustum.

The closure means 40 according to the invention is formed as a plug closure means. The plug closure means 40 comprises a plug portion 46 and a plate-like portion 42. Both portions 42 and 46 are connected to one another via an integral leg 44. Through-holes 43 are provided in the plate-like portion 42.

The plug closure means 40 and the piston 22 serve for closing the front and rear ends of chamber 12 which has already been filled with a substance to be dispensed (not shown). In this state of the filled chamber 20, piston 22 is inserted into the rear end of chamber 12 and the plug portion 46 of the one-piece plug closure means 40 is inserted into the outlet opening 13 of the container 10. In this state, the filled container 12 can be stored and transported separately from the outlet piece 30. Alternatively, the outlet piece 30 can already be mounted to the container 12, however, the outlet piece 30 should only be slid over such a short distance upon the container 12 that the outlet opening 13 is still completely shut off by means of the plug portion 46. In an alternative embodiment different from the system of FIG. 1, the piston 22 can also be provided in the form of a separate component not connected to the piston rod 23 of the piston unit 20.

When using the ampoule according to FIG. 1, the outlet piece 30 is fully mounted to the upper portion of the container 10, whereby the plug closure means 40 is displaced or slid in a direction towards the interior of chamber 12 until the plate-like portion 42 engages the front end wall of container 10. In this state, the outlet opening 13 of container 10 is no longer closed by the plug portion 46 so that the substance (not shown) contained in chamber 12 can be discharged. For expelling the substance, the piston unit 20 is manipulated and thereby the substance is urged through the outlet opening 13 and the through-holes 43 of the plug closure means 40 aligned with the outlet opening 13, into the space 33 of the outlet piece, and to the exterior of the ampoule via the discharge passage 34.

The substance can also be expelled by moving together the container 10 and the piston unit 20 in telescope-like manner. For this purpose, the fingers of one hand engage an extension 16 at the rear end of container 10 and at the same time a plate-like extension 26 of the piston unit 20. Proper means ensure that the outlet piece 30 is not displaced in the forward direction in relation to container 10 and that the substance does not escape at the rearward end of outlet piece 30. One skilled in the art can choose convenient means for this purpose, such as integrally formed projections or rims, press connections, screw connections and bayonet-like connections, locking connections and the like. Furthermore, it is possible to engage shoulder 31 of the outlet piece 30 instead of extension 16 for moving together the components of the ampoule in a telescope-like manner.

The second embodiment of the present invention shown in FIGS. 2 to 4 distinguishes from the ampoule of FIG. 1 essentially in that the upper portion of the container, the plug closure means and the outlet piece are formed in a different manner. The piston unit is not shown in this embodiment. As in the first embodiment, the container 210 of the second embodiment comprises a chamber 212 for receiving a substance (not shown) to be dispensed. An outlet opening 213 of chamber 212 is provided in a front wall 217 at the front end of container 210. A neck 218 protruding in forward direction is integrally formed with the front wall 217 and surrounds the outlet opening 213 at a distance therefrom.

The plug closure means 240 comprises a plug portion 246 for closing the outlet opening 213 at its rear end. The plug closure means 240 comprises at its front end a portion 242 being widened in a flange-like or plate-like manner. At least one cross opening 245 is provided within the plug closure means 240 above the plug portion 246 thereof. The cross opening 245 communicates with a longitudinal hole 243 which extends in the forward direction.

The outlet piece 230 consists of a tube-like front portion 232 and a plug-like rear portion 236. The front portion 232 and the adjoining rear portion 236 surround a discharge passage 234 which extends in longitudinal direction of the outlet piece 230. The outlet piece 230 can be provided separately from the container 210 during storage or transport or can, alternatively, be inserted with its rear portion 236 into the neck 218 such that the plug closure means 240 is still in its closed position according to FIG. 3.

FIG. 3 shows the ampoule according to the second embodiment in a state in which the outlet opening 213 of the filled container 210 is closed by means of the plug portion 246 of the plug closure means 240. In this transport or storage condition of the ampoule, the plug closure means 240 is entirely received within the space defined by neck 218. By virtue of this design the danger of unintentionally displacing the plug closure means 240 into the open position is substantially reduced. Preferably, also the inner circumferential wall of neck 218 is used for guiding the front flange-like portion 242 of the plug closure means.

FIG. 4 shows the ampoule according to the second embodiment in an activated state where the substance (not shown) contained in chamber 212 can reach the discharge passage 234 of outlet piece 230 via the plug closure means 240 having been displaced into its open position. The open position shown in FIG. 4 is achieved by inserting the outlet piece 230 into neck 218 until the flange-like portion 242 of the plug closure means 240 engages the upper surface of the front wall 217 of the container 210 and until the cross opening 245 comes into fluid communication with the interior of chamber 212.

Moving together the components of the ampoule according to FIGS. 2 to 4 in a telescope-like manner can be accomplished in a manner corresponding to the manner having been described in connection with the ampoule according to FIG. 1. The embodiment of FIGS. 2 to 4 is also provided with suitable means for holding the outlet piece 230 and, together therewith, the plug closure means 240 in place as shown in FIG. 4 when the substance is dispensed.

A third embodiment shown in FIGS. 5 to 8 is a multichamber-ampoule. The multichamber-ampoule also essentially consists of four parts, namely a container 110, a piston unit 120, an outlet piece 130 and a closure means 140. Two separate cylindrical chambers 112 and 114 are provided within container 110, and extend in the longitudinal direction of container 110. Chambers 112 and 114 are open at their rear ends and each have at their respective front ends an outlet opening 113 and 115, respectively. A radially outward extending part 116 is integrally connected to the rearward end of container 110.

The piston unit 120 comprises two separate circular cylindrical pistons 122 and 124, as well, as two corresponding piston rods 123 and 125 arranged in parallel and at a distance to one another. The rear ends of the piston rods are connected by means of a plate 126. The outer diameter of the pistons 122, 124 essentially corresponds to the inner diameter of the circular cylindrical cross section of chambers 112 and 114 as in case of the previous embodiments. After having been inserted into the chambers, the pistons 122 and 124 engage the chamber walls as tight as possible, particularly fluid-tight, such that the pistons are still displaceable in the longitudinal direction of the chambers.

The outlet piece 130 comprises a front portion 132 and a rear portion 136. The front portion 132 is formed in a tube-like manner and surrounds a discharge passage 134 with a relatively small circular cross section. The rear portion 136 of the outlet piece 130 has a substantially larger cross sectional dimensions in comparison to the front portion 132 and defines an inner space 138 which is open to the rear and merges into the discharge passage 134 in the forward direction.

The container 110 comprises, in a direction orthogonal to its longitudinal axis, an outer cross sectional area which substantially corresponds to the inner cross sectional area of hollow space 138. Thereby, the outer wall of container 110 having been inserted into the inner space 138 engages the circumferential wall of the outlet piece 130 defining the inner space 138 as tightly as possible, particularly in a fluid-tight manner. Between the smaller diameter, tube-like front portion 132 and the comparatively wider rear portion 136 with larger sectional dimensions, the outlet piece 130 comprises an essentially radially extending shoulder 131. Shoulder 131 defines a space 133 in the form of a shallow truncated cone establishing an intermediate or transition space between the wider inner space 138 and the relatively narrow discharge passage 134.

Shoulder 131 is, according to FIG. 5, sloped and can offer a contact surface for manually actuating the device by applying finger pressure. When doing so, a finger of the same hand can be applied to piston unit 120 for expelling the substances (not shown) contained in chambers 112 and 114 by means of moving together the piston unit and the container 110 having been inserted into the outlet piece 130 in telescope-like manner. A radially outwardly extending portion 137 can be provided at the rear end of outlet piece 130 for a better manipulation.

The closure means 140 is provided in the form of a multiplug-closure means and serves for tight closure of the outlet openings 113 and 115 of container 110. The multiplug-closure means 140 comprises a plate 142, the outer cross sectional dimensions of which substantially correspond to those of container 110 and the cross sectional dimension of inner space 138, respectively. Plate 142 comprises two half-circular through-holes 143. Two legs 144 are integrally formed with plate 142 and suspend adjacent to the through-holes 143 therefrom. The legs 144 have a half-circular cross section and merge into a cylindrical plug portion 146 at their lower ends. The plug portions 146 serve for fluid tight closure of the outlet openings 113 and 115 and, therefore, have an outer diameter which is correspondingly adapted to the inner diameter of these openings 113 and 115.

FIG. 6 shows container 110 ready to use for storing or transport. In this condition the outlet openings 113 and 115 of chambers 112 and 114 are closed by means of the plug portions 146 of the single piece multiplug-closure means 140 in a fluid-tight manner. The rear ends of the chambers 112 and 114 are shut off by the pistons 122 and 124 inserted therein. The multiplug-closure means 140 and the pistons 122 and 124 thus define two fluid and liquid-tight spaces within chambers 112 and 114. The substances (not shown) to be mixed are provided in these spaces for mixing when being discharged.

Container 110 of FIG. 6 shown in a ready to use state can be stored and transported separately from outlet piece 130. Preferably, however, the container of the third embodiment of the invention according to FIGS. 5 to 8 is stored and transported in a condition in which the ready-to-use container 110 is already inserted into the inner space 138 of outlet piece 130. This insertion is, however, limited and both parts can be moved together only until the multiplug-closures means 140 is still spaced from shoulder 131 or only slightly engages shoulder 131. Thereby, it must be ensured that the multichamber-ampoule is not activated for use.

Immediately before using the multichamber-ampoule of FIGS. 5 to 8, activation is accomplished by fully inserting container 110 into the inner space 138 of outlet piece 130 whereby the multiplug-closure means 140 is urged against shoulder 130. When doing so, the plug portions 146 move from the outlet openings 113 and 115 into the inner space of chambers 112 and 114 and plate 142 engages the upper front face of container 110 as shown in FIG. 8. As chambers 112 and 114 have slightly larger bores than the outlet openings 113 and 115 or, in other words, the outer diameter of the plug portions 146 is smaller than the inner diameters of chambers 112 and 114 below outlet openings 113 and 115, the upper ends of chambers 112 and 114 are no longer closed. The substances (not shown) contained in chambers 112 and 114 can thus reach outlet openings 113, 115 and be expelled via the adjoining through-holes 143 and the outlet or mixing chamber 133 of outlet piece 130.

Extension 116 provided at the rear end of container 110 facilitates activation by means of fingers and a finger of the same hand can engage radially extending portion 137 or shoulder 131 of outlet piece 130. Those skilled in the art can of course modify the form of the extensions and portions 116, 137, respectively, in order to provide the desired function. For example, it is possible to provide only a single protrusion at one position of the respective circumferential wall or two protrusions opposite to one another or angularly displaced with respect to one another.

After having activated the ampoule, the pistons 122 and 124 are pushed in the forward direction into chambers 112 and 114 by means of plate 126 and piston rods 123 and 125 connected thereto in order to expel the substances. When doing so, the substances are urged into mixing space 133 and discharged via the discharge passage 134 as shown by the arrows in FIG. 8. It is possible to provide a static mixer (not shown) within discharge passage 134. Instead of using separate pistons 122 and 124 and associated piston rods 123 and 124, a one-piece piston unit can also be used.

Advantageously, after having activated the ampoule according to the condition shown in FIG. 8, plate 142 being clamped between the front wall of container 110 and the inner surface wall of shoulder 131 guarantees that the plug portion 146 can no longer shut off the outlet openings 113 and 115 during the upwards movement of the pistons 122 and 124 because the legs 144 retain the plug portions 146 at a distance from the outlet openings 113 and 115. At the same time, plate 142 promotes the sealing between the outer wall of container 110 and inner wall of outlet piece 130. To improve the sealing effect, the multiplug-closure means 140 can be made from a rubber-like material. There are many possible modifications of the multiplug-closure means 140 e.g. regarding the geometry of plate 142, of the through-holes 143 and legs 144, which modifications can be made by those skilled in the art.

FIGS. 9 to 16 show a fourth embodiment of the invention which also concerns a multichamber-ampoule. The four essential parts of this ampoule consist of a container 310, a piston unit 320, an outlet piece 330 and a multiplug-closure means 340. The container 310 comprises two tube-like chambers 312 and 314 arranged in parallel to one another and being open at their rear ends over the entire cross section. A laterally or radially extending plate is integrally formed to the circumferential outer walls of the rear ends of chambers 312 and 314 and protrude beyond chambers 312 and 314 in the form of one or a plurality of protruding extensions 316. The forward ends of chambers 312 and 314 are connected to each other via a front wall 317 which comprises an outlet opening 313 for chamber 312 and an outlet opening 315 for chamber 314. An annular neck 318 is integrally formed to the front wall 317. Neck 318 surrounds the outlet openings 313 and 315 such that the circular outlet openings 313 and 315 contact the circular inner circumferential wall of neck 318 in longitudinal direction of container 310.

The piston unit 320 comprises two pistons 322 and 324 which are provided separately. Again piston unit 320 comprises two piston rods 323 and 325 the rear ends of which are connected by means such as an integral plate 326 and the like.

The outlet piece 330 has a cylindrical rear portion 336. Radially outwardly protruding extensions 337 are integrally formed at the front end of portion 336. The rear end of cylindrical portion 336 merges into an oblique circumferential wall 331 which extends inwardly and towards the front end of the outlet piece 330. The circumferential wall 331 defines a mixing space 333 provided in the form of a truncated cone which is open at its rear end. The narrower front end of circumferential wall 331 merges into a tube-like section protruding from the front end of the rearward portion 336 and forming a front portion 332 of the outlet piece 330. A discharge passage 334 extends within the front portion 332 in the longitudinal direction of the outlet piece 330. The rearward end of the discharge passage 334 and the front end of mixing space 333 communicate.

The multiplug-closure means 340 consists of two cylindrical plug portions 346 integrally connected to a common connecting plate 342 via legs 344. Two through-holes 343 are formed in plate 342 and aligned with the plug portions 346.

FIG. 15 shows a state in which chambers 312 and 314 are each filled with a substance (not shown), and are closed by means of the pistons 322 and 324 as well as the plug portion 346 of the multiplug-closure means 340. In this transport or storage condition the multiplug-closure means 340 is entirely housed within the neck 318 and guided by the inner circumferential wall of neck 318. For this purpose, connecting plate 342 is preferably circular and has an outer diameter which substantially corresponds to the inner diameter of neck 318. The outlet piece 330 can already be inserted into neck 318 in this transport and storage condition of the filled container 310 according to FIG. 15, but again insertion has to be limited so that the outlet openings 313 and 315 remain closed by plug portions 346.

For activating the ampoule, outlet piece 330 is inserted into neck 318 until the connecting plate 342 abuts the front wall 317. This activated state is shown in FIG. 16. The plug portions 346 then clear the through-holes 313 and 315 and the through-holes 343 of the multiplug-closure means 340 are aligned with the through-holes 313 and 315. When moving the container 310 and the piston unit 320 together in a telescope-like manner, the substances contained in chambers 312 and 314 escape into mixing space 333, are mixed therein, and are then expelled via the discharge passage 334.

As in the previous embodiments, this embodiment comprises means for holding the outlet piece 330 in position (FIG. 16) when discharging the substances. This can, for example, be accomplished by firmly fitting the rear portion 336 of the outlet piece 330 within neck 318. In the case of substances having a relatively great consistency (e.g. pasty substances), a positive locking or form-locking connection between container and outlet piece is advantageous. Again a static mixer (not shown) can be provided in discharge passage 334.

Figure 17:
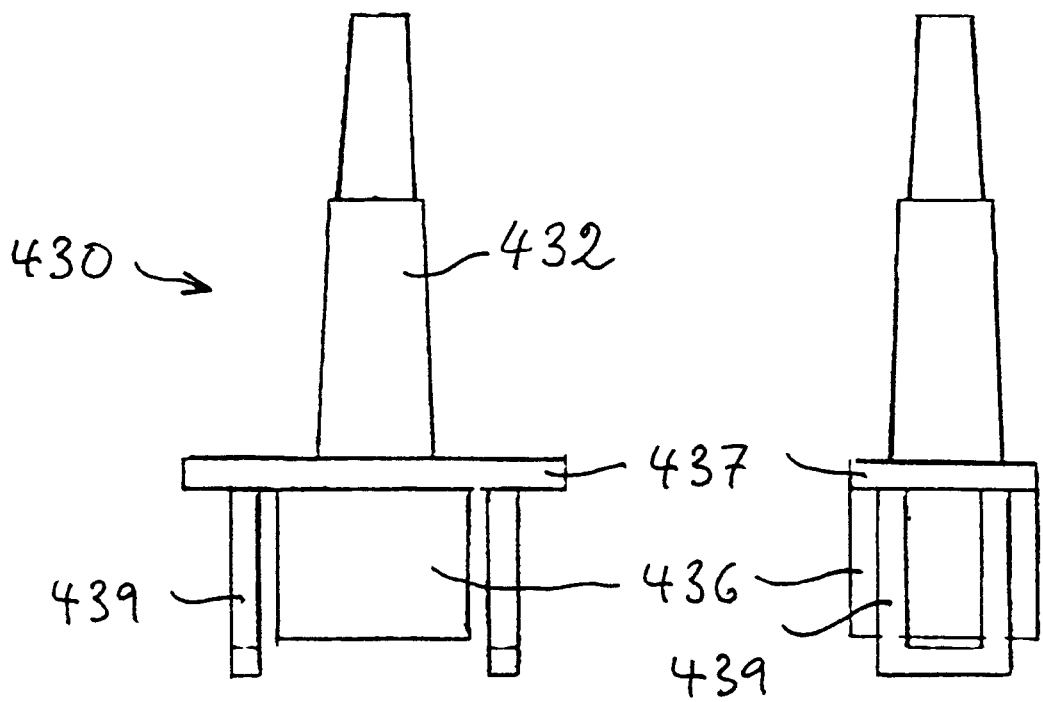
FIG. 17 is an exploded view of essential parts of a fifth embodiment of the invention.

FIG. 17 shows a fifth embodiment of the present invention having a preferred positive locking or form-locking connection between a container and an outlet piece of the ampoule according to the invention. The fifth embodiment shows a multichamber-ampoule similar to the ampoule of the fourth embodiment. However, it has to be noted that the special features of the fifth embodiment can also be applied to other embodiments of the invention.

Figure 18:
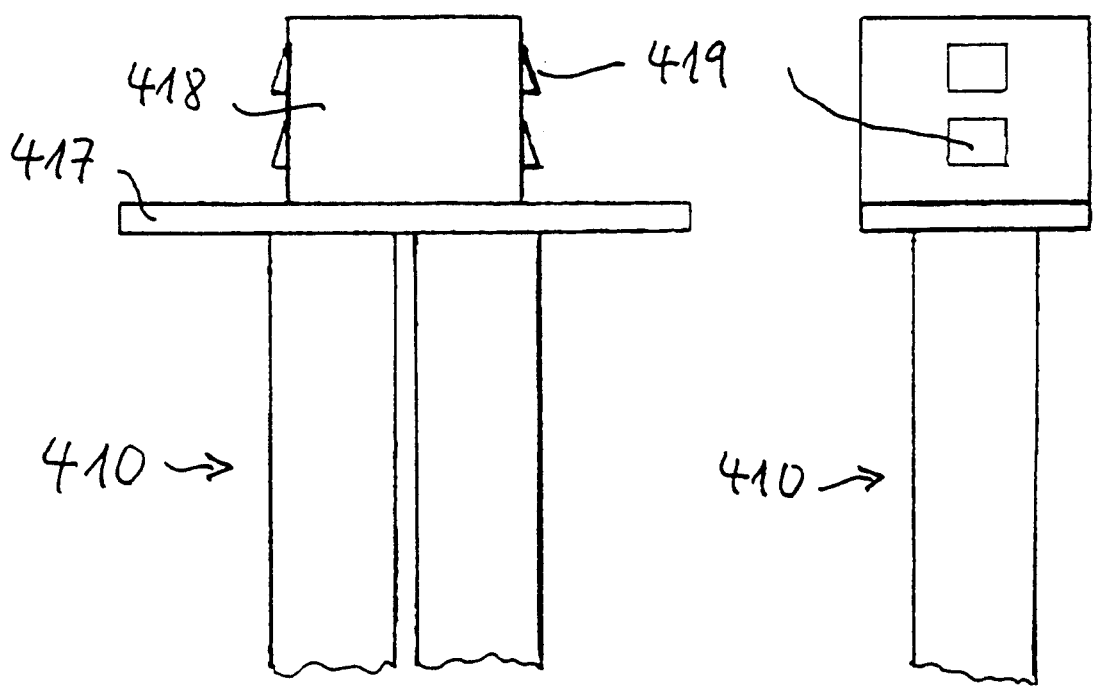
FIG. 18 is an exploded view of essential parts of the fifth embodiment according to FIG. 17 showing a side view of the ampoule of FIG. 17 in which the ampoule is rotated around its longitudinal axis by 90° in comparison to FIG. 17.

FIGS. 17 and 18 show the upper portion of the container 410 and an outlet piece 430. Container 410 comprises two cylindrical chambers with a front wall 417 integrally formed thereto. Again a neck is integrally formed to the side of front wall 417 opposite to the chambers. The neck 418 surrounds the outlet openings of the chambers as disclosed above in the fourth embodiment. The outlet piece 430 has a tube-like front portion 432 and a plug-like rearward portion 436. As in the fourth embodiment, a discharge passage extends in the longitudinal direction of the outlet piece and the discharge passage merges into a mixing chamber in the form of a truncated cone.

Two detents or latches 419 are provided on the outer circumferential wall of neck 418 at two different heights in such a way that each detent has an opposite detent at the same height. The outlet piece 430 has a laterally extending added piece 437. Resilient notch tongues or hooks 439 are integrally formed to the added piece 437. The tongues or hooks 439 are radially spaced from the rearward portion 436 and are diametrically opposite from one another. Furthermore, they extend in rearward direction. The outlet piece 430 can be locked to container 410 in a first forward position during a storage or transport condition of the container 410 being filled with substances and closed by a multiplug-closure means. In this forward locking position, the locked outlet piece 430 has not yet displaced the multiplug-closure means so that the through-holes of the chambers remain closed. In this condition, the hooks 439 engage the upper detents 419.

The outlet piece 430 is moved in a direction towards the container 410 into the rearward locking position for activation of the ampoule. When doing so, the outlet openings of the chambers of container 410 are cleared and a fluid communication between the inside of the chambers and the discharge passage of the outlet piece 430 is established, as described above in the previous embodiments. In this discharge condition, the hooks 439 engage the lower detents 419 so that the outlet piece 430 is held in position relative to the container when pushing forward the pistons (not shown).

The individual components of the ampoule are preferably made from a thermoplastics material, such as polyethylene. The characteristics of polyethylene required for preparing the ampoule can be varied according to the particular application of the individual parts of the ampoule and the manner of cooperation thereof.

The particular features of the individual embodiments described above can, in general, be applied to all embodiments. Obviously, many modifications and variations of the present invention are made possible in the light of the above teachings. Accordingly, each one of the embodiments can be modified such that the piston units are reduced to pistons 22, 122, 124, 322, 324 and that discharge of the fluid(s) is effected by means of a device creating a sub-atmospheric pressure above the fluid. Such a device can be mounted to the respective outlet piece 30, 130, 330 or, alternatively, the outlet piece can be modified to fulfill the function of creating a sub-atmospheric pressure. The handling of the ampoule will not be changed regarding the activation step explained above. Merely the step of expelling the substance(s) will, instead of moving the piston rods, consist in creating a sub-atmospheric pressure above the fluid levels in chambers 12, 112, 312 and discharging the substances by virtue of suction. As the pistons are movable within chambers 112, 312, it is advantageously guaranteed that both substances are equally mixed even in the case of substances which substantially differ regarding their viscosity and the like.

Furthermore, the cross-sectional areas of the chambers may be of different shape. for example, oval, half-circular or the like. The same holds true for the plugs, through-holes and openings.

What is claimed is:

1. A multichamber-ampoule for dispensing a mixture consisting of a plurality of substances, comprising:
    a container (110; 310) having at least two chambers (112; 114; 312, 314) therein being arranged in parallel to each other for storing said substances and having adjacent outlet openings (113; 115; 313, 315);

a piston (122, 124; 322, 324) provided in each chamber (112, 114; 312; 314) so as to be matingly displaceable in a longitudinal direction of the chamber;

an outlet means (130; 330) which can be connected to the container such that a fluid communication is established between the outlet openings (113; 115; 313, 315) of the chambers and an inlet portion of a discharge passage (134; 334) of said outlet means; and a plurality of plug closure means (140; 340) corresponding to the plurality of outlet openings (113; 115; 313, 315) of the chambers, each plug closure means being insertable in a fluid-tight manner into its associated outlet opening (113; 115; 313, 315) and, when said plug closure means (140; 340) have been fluid-tightly inserted into the outlet openings (113; 115; 313, 315), they are displaceable by said outlet means (130; 330) connected to the container (110, 310) in a direction towards the interior of their associated chambers (112; 114; 312, 314) from a closed position into an open position in which a fluid communication is provided between the interior of the chambers (112; 114; 312, 314) and the inlet portion of the discharge passage (134; 334) of the outlet means via said outlet opening (113; 115; 313, 315) of the chamber, said plug closure means (140; 340) having retaining means (142; 342) retaining said plug closure means (140; 340) in said open position.

2. The multichamber-ampoule according to claim 1 wherein the ends of the plug closure means (146; 346) opposite to the chambers (112, 114; 312; 314) are integrally connected to a common connecting portion (142; 342) forming therewith a multiplug-closure means (340), said outlet means (130; 330) engages said common connecting portion (142; 342) when being connected to the container (110; 310).

3. The multichamber-ampoule according to claim 1 wherein an end portion of the container, which carries the plug closure means, is insertable into an inner space (138) of the outlet means (130) in a fluid-tight manner, which inner space (138) adjoins the inlet portion of the discharge passage (134).

4. The multichamber-ampoule according to claim 1 wherein a neck (318) is formed at the end portion of the container (310), which carries the plug closure means (346), which neck (318) surrounds the adjacent outlet opening (315, 315) of the chambers and servers as connecting means for connecting the outlet means (330) thereto.

5. The multichamber-ampoule according to claim 4 wherein the outlet means (330) comprises a portion (336) which is provided at the inlet portion of the discharge passage (334) and which immerses into the neck (318) when connecting the outlet means (330) to the container (310).

6. The multichamber-ampoule according to claim 4 wherein the connecting portion (342) of the multiplug-closure means (340) is guided in the neck (318).

7. The multichamber-ampoule according to claim 1 wherein at least two plug closure means (146; 346) are provided which are integrally connected to a common connecting portion (142; 342) forming therewith a multiplug-closure means (340).

8. The multichamber-ampoule according to claim 1 wherein the outlet means (130; 330; 430) is connectable to the container (110; 310; 410) by means of a positive and/or frictional connection.

9. The multichamber-ampoule according to claim 8 wherein the outlet means (430) is connectable to the container (410) by locking.

10. The multichamber-ampoule according to claim 1 wherein, in a first connecting position of the outlet means (130; 330) to the container (110; 310), said plug closure means remain in said closed position, and wherein, when said outlet means is displaced from said first connecting position into a second connecting position, said plug closure means (146; 346) are displaced from said closed position into said open position.

11. The multichamber-ampoule according to claim 1 wherein the substances are dispensed by suction effected by means of creating a sub-atmospheric pressure above the substances to be dispensed.

* * * * *